(12) United States Patent
Gibson

(10) Patent No.: US 6,224,587 B1
(45) Date of Patent: May 1, 2001

(54) STEERABLE CATHETER

(75) Inventor: Charles A. Gibson, Malden, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/447,440

(22) Filed: Nov. 22, 1999

(51) Int. Cl.⁷ .................................................. A61M 25/01
(52) U.S. Cl. ............................................................ 604/528
(58) Field of Search .................................. 604/528, 282, 604/96, 523–525, 532, 95.01–95.05

(56) References Cited

U.S. PATENT DOCUMENTS 5,879,499 * 3/1999 Corvi .................................... 156/175
5,910,129   6/1999 Koblish et al. ........................ 604/95
5,916,147   6/1999 Boury ................................... 600/146

* cited by examiner

*Primary Examiner*—Sharon Kennedy
*Assistant Examiner*—Ann Y. Lam
(74) *Attorney, Agent, or Firm*—Darby & Darby

(57) ABSTRACT

A medical device including an elongated shaft that is twisted through a predetermined angle. One or more lumen are formed in the shaft and twist through the predetermined angle as well. A pull wire extends through one of the lumen and attaches to a distal portion of the elongated shaft at an off-axis location. By tensioning the pull wire, the medical device can assume various complex curves, depending on the degree of twist imparted to the shaft.

19 Claims, 2 Drawing Sheets

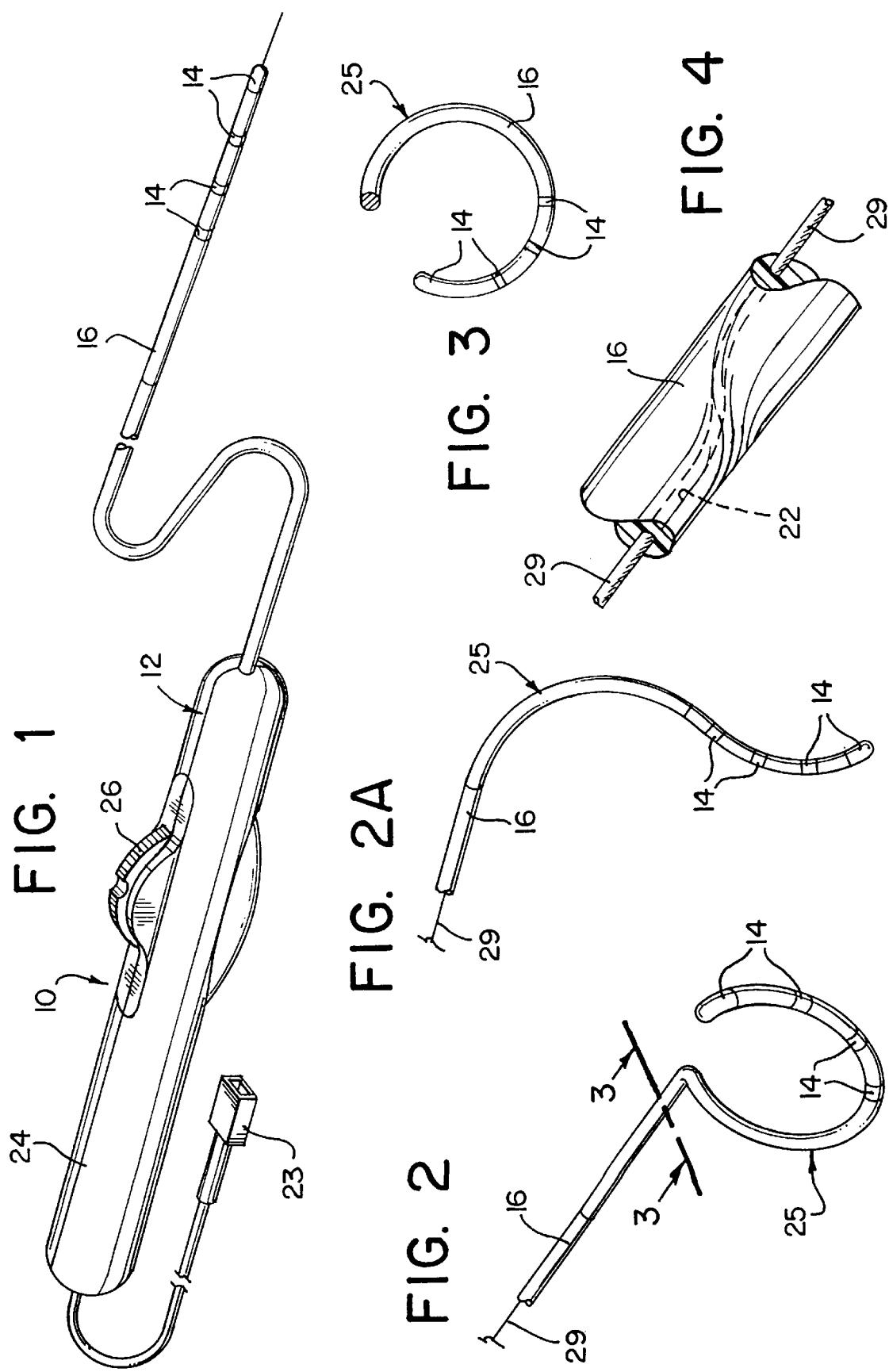

FIG. 5
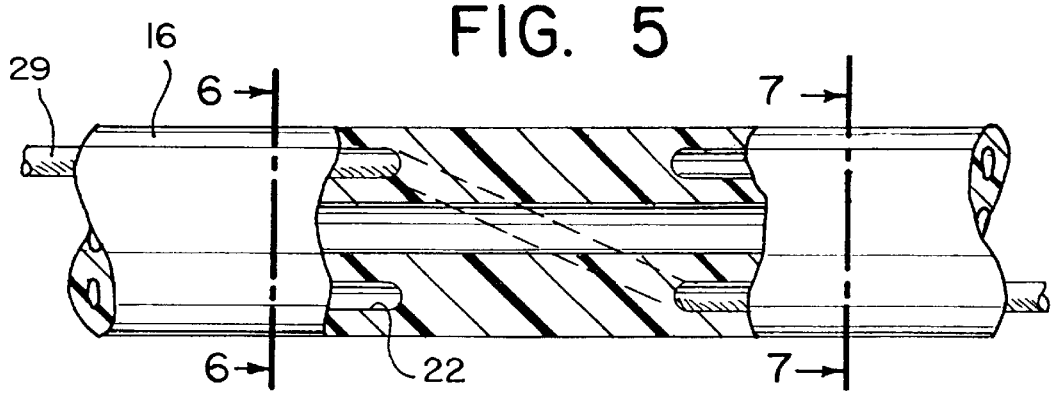
FIG. 6     FIG. 7
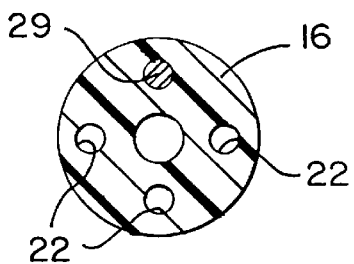 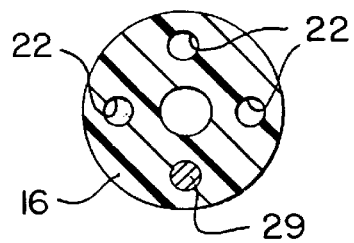
FIG. 8
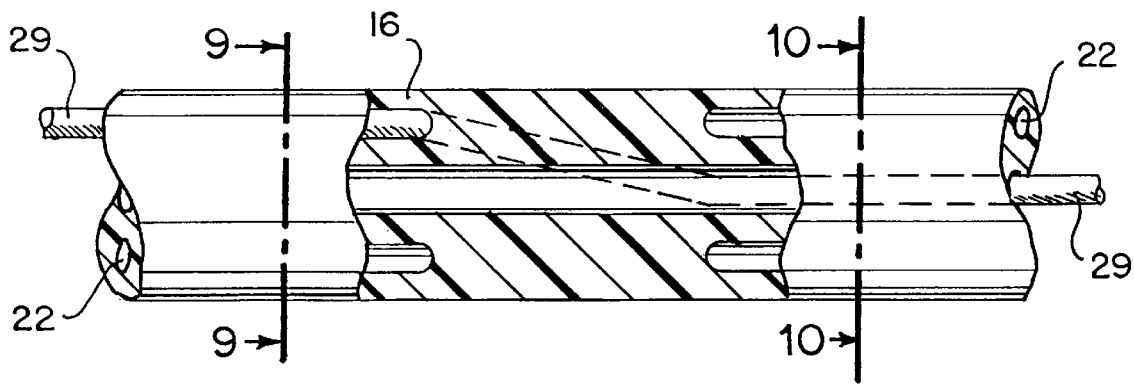
FIG. 9     FIG. 10
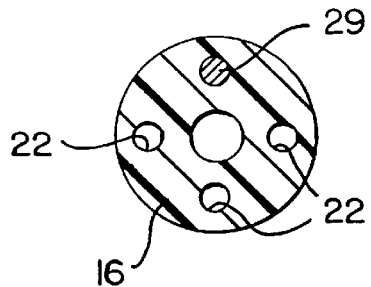 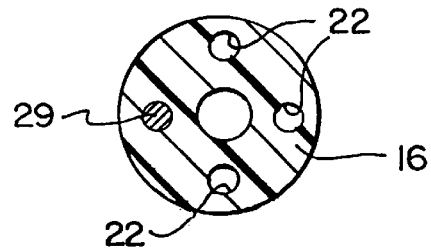

STEERABLE CATHETER

FIELD OF THE INVENTION

The present invention generally relates to the field of steerable catheters. More specifically, the invention is directed to a steerable catheter with a specially configured shaft and which includes a single pull wire arranged to allow the catheter to achieve various complex curvatures.

BACKGROUND OF THE INVENTION

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like, as is well known to those skilled in the art.

In order to manipulate the catheter through a patient's vasculature, the catheter must be flexible. In addition, such catheters are preferably steerable, so that the clinician may temporarily impart a desired curve to the catheter from a remote location in order to pass through curved areas within a patient. A conventional steerable catheter includes one or more pull wires which extend through the catheter shaft, and connect to the catheter adjacent the distal end of the catheter at an off-axis location. The pull wires connect to a control knob or knobs, slide actuator, or other suitable manipulating member that is mounted in a control handle. A form of such a catheter is disclosed in U.S. Pat. No. 5,383,852 to Stevens-Wright and assigned to the assignee of the rights in the present invention, the disclosure of which is hereby expressly incorporated by reference.

While such catheters have gain widespread acceptance in the industry, they nevertheless suffer from certain shortcomings. One shortcoming is that to achieve relatively complex curves, those catheters require multiple pull wires which extend through different lumen and which connect to the catheter at different anchoring points. In addition, the pull wires each require a separate manipulating member to tension the respective pull wires. Thus, in a conventional steerable catheter, a relatively large amount of space is occupied by the steering subsystem, which limits the amount of space available for other components.

In addition, ablation catheters typically must assume various curves so that the ablation electrodes carried on the catheter will come into contact with a patient's tissue at selected locations. Thus, for that additional reason, catheters should be able to assume complex curves.

Others have designed catheters that achieve complex curves, for example, three-dimensional curves. One such catheter requires a secondary anchoring point, and a catheter shaft having a segment of intermediate stiffness and a more flexible segment, such that when the pull wires are tensioned, the catheter shaft assumes some relatively complex curve. However, to achieve such a curve, the catheter requires an intricate structure.

Accordingly, it will be apparent that there continues to be a need for a steerable catheter which can achieve relatively complex curves to facilitate manipulation of the catheter through a patient's vasculature and to an intended site. Moreover, the needs exists for such a catheter with a steering subsystem that occupies a relatively small amount of space within the catheter to accommodate a relatively large number of other components. The instant invention addresses these needs.

SUMMARY OF THE INVENTION

Briefly, the present invention is in the form of a catheter that includes a catheter shaft which is permanently twisted during formation through a selected angle and at a predetermined location on the shaft. The catheter shaft includes one or more lumen, which rotate through the selected angle at the predetermined location. A pull wire is provided and extends through one of the lumen, including through the twisted region, and attaches to the inside of the catheter shaft adjacent the distal end thereof. By tensioning the pull wire, the catheter can assume various complex curves, depending on the selected angle through which the catheter shaft is rotated and the location of the twist. A proximal segment of the catheter can assume a curve in a first plane, while a distal segment of the catheter can assume a curve in a different plane, thereby achieving a three-dimensional curvature with a single pull wire.

Thus, according to one illustrative embodiment, the present invention is directed to a medical device including: an elongated shaft having at least one lumen extending through the shaft, the shaft being formed at a predetermined region with a twist, whereby the lumen extends through the shaft in a non-linear manner; a pull wire extending through the at least one lumen; and means for tensioning the pull wire to impart a desired curve to the shaft.

In another illustrative embodiment, the invention is directed to a medical device that includes a handle with a pull wire tensioning member that is manipulable relative to the handle; an elongated shaft including at least one lumen extending through the shaft, the shaft being formed at a predetermined region with a twist, whereby the lumen extends through the shaft in a non-linear manner; and a pull wire extending through the at least one lumen, the pull wire being connected to the pull wire tensioning member, whereby manipulation of the pull wire tensioning member tensions the pull wire to induce a curvature in the shaft.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 1 is a perspective view of a steerable medical device including a steering subsystem according to one illustrative embodiment of the present invention;

FIG. 2 is a fragmented perspective view of the medical device of FIG. 1 with the distal end thereof manipulated to assume a curved configuration;

FIG. 2A is a fragmented perspective view of another embodiment of the present invention;

FIG. 3 is a cross-sectional view taken along the line 3—3 of FIG. 2 and looking in the direction of the arrows;

FIG. 4 is an enlarged perspective view of a portion of the medical device of FIG. 1;

FIG. 5 is a fragmented, partially sectional view of the medical device of FIG. 1;

FIG. 6 is a cross-sectional view taken along the line 6—6 of FIG. 5;

FIG. 7 is a cross-sectional view taken along the line 7—7 of FIG. 5;

FIG. 8 is a fragmented, partially sectional view similar to FIG. 5 and showing another embodiment of the present invention;

FIG. 9 is a cross-sectional view taken along the line 9—9 of FIG. 8; and

FIG. 10 is a cross-sectional view taken along the line 10—10 of FIG. 8.

DETAILED DESCRIPTION OF THE PREFERRED EMBODIMENTS

Referring now to the drawings, and particularly to FIG. 1, there is shown a medical device 10 according to one illustrative embodiment of the present invention. In one illustrative embodiment, the medical device 10 includes a steering subsystem, generally designated 12, which is operative to impart a desired curve to the catheter. In one illustrative embodiment, the catheter includes one or more electrodes 14, one or more of which may be slidably mounted over an elongated tubular shaft member 16 of the device 10 and which are selectively movable relative to the shaft in either a distal or proximal direction along the shaft 16. Thus, for example, the device 10 may be manipulated through a patient's blood vessels by means of the steering subsystem 12 until the electrodes 14 are disposed at desired locations within the patient's body. The electrodes may then be used for ablation, for sensing electrical activity within the heart, or any other suitable function.

Referring to FIG. 1, the medical device 10 in one illustrative embodiment is in the form of a catheter, for example, an ablation catheter, therapeutic catheter, mapping catheter, or other diagnostic catheter. It will be apparent that the medical device 10 of the present invention can take many different forms, such as any medical device having an elongated insertion member to be inserted into a patient's body. In the illustrative embodiment, the catheter includes the catheter shaft 16, which is preferably a flexible shaft which can be manipulated through a patient's blood vessels and to a site of interest within the patient's body, as is described in greater detail below. The catheter shaft defines a plurality of interior lumen 22 (FIGS. 6, 7, 9, and 10) which are formed having predetermined cross-sectional dimensions for passing various components through the respective lumen, as is described in greater detail below.

In one embodiment, the medical device 10 includes a control handle 24 for manipulating the steering subsystem 12 (FIG. 1). The catheter handle may take many different forms. One suitable form of control handle is shown in FIG. 1 and is disclosed in greater detail in U.S. Pat. No. 5,462,527 to Stevens-Wright, the disclosure of which is hereby expressly incorporated by reference as if fully set forth herein. Briefly, the control handle includes a rotatable control knob 26 which is mounted in the handle and may be rotated relative to the control handle. The control knob is preferably connected to a component of the steering subsystem 12, as is described in greater detail below. Another suitable form of control handle is disclosed in U.S. Pat. No. 5,611,777 to Bowden et al., which is expressly incorporated herein by reference.

The control handle 24 is preferably connected to a suitable electrical connector 23, which connects to a suitable power supply (not shown) to provide ablation energy to the various electrodes 14, or alternatively to diagnostic equipment (not shown) to transmit sensing signals generated by the catheter electrodes, as is well known in the art and described in greater detail below.

According to one illustrative embodiment of the invention, the control knob 26 is fixedly engaged to a proximal end of a pull wire 29 which extends through the inside of the shaft 16 and is connected to the distal end portion of the shaft, preferably at an off-axis location. As such, tension applied to the pull wire causes the shaft 16 to curve in a predetermined direction or directions.

Referring to FIGS. 2, 3, 4, and 8 through 10, there is shown one illustrative embodiment of the invention. The single pull wire 29 extends from the control knob 26 through a first lumen 22 to a twisted region 25 of the shaft 16. In the illustrated embodiment, the twisted region is twisted through an angle of 90°. The pull wire transitions through the 90° angle and continues through the same lumen 22. The pull wire connects to the catheter at an off-axis location adjacent the distal end thereof.

Thus, when tension is applied to the pull wire 29, a distal portion of the catheter shaft 16 assumes a generally C-shaped curve, with the proximal-most portion of the curve defining the twisted region 25 of the catheter shaft. In this manner, the catheter shaft 16 assumes a three-dimensional curve through the use of a single pull wire. The remaining lumen extending through the catheter shaft may be used for passing other components, such as lead wires and the like, from the proximal end of the shaft to the distal end.

Preferably, the proximal and distal portions of the catheter shaft 16 separated by the twisted region 25 are formed of different compositions having different durometers, which allows for different curves for the respective regions from the single pull wire 29. Thus, when tension is created in the pull wire 29, the portion formed of softer material will curve to a greater extent than the more rigid portion. As such, by selecting the respective durometers of the proximal and distal portions, the extent to which the respective portions curve can be determined. Preferably, the catheter shaft 16 is formed of a relatively rigid material up to the twisted region, such that when the pull wire is tensioned, only the portion of the catheter shaft distal to the twisted region curves, and the majority of the shaft remains generally linear (FIG. 2).

Referring now to FIGS. 2A, and 8 through 10, there is shown a second illustrative embodiment of the invention. In this embodiment, the shaft 16 is twisted through an angle of 90° and the pull wire 29 extends through one of the lumen 22 within the shaft and connects to the shaft at an off-axis location adjacent the distal end of the shaft.

Thus, when the pull wire is tensioned by manipulating the control knob 26, the proximal region of the shaft (i.e., a region proximal to the twisted region) will curve in a first direction and the distal region (i.e., the region distal to the twisted region) will curve in the opposite direction (i.e., the two curves lie in the same plane but face in directions 180° apart) (FIG. 2A).

It will be apparent to those skilled in the art that the pull wire 29 may be extended through a lumen that is twisted through some angle other than 90° or 180°. When the pull wire has a 180° transition through the twisted lumen, the corresponding curves are coplanar, as is shown in FIG. 2A. However, when the pull wire transition is less than 180°, the corresponding curve imparted to the catheter shaft assumes a three-dimensional configuration. Thus, depending on the desired configuration, the degree of twist imparted to the lumen 22 can be through any desired angle, such as 30°, 45°, 60°, or any other angle.

In addition, while in the illustrative embodiments, the catheter shaft 16 is formed with only a single twisted region 25, it will be understood by those skilled in the art that the shaft may be formed with two or more twisted regions at respective spaced apart locations along the catheter shaft. The twisted regions may each be rotated through the same angle, or each may be rotated through a different angle. The pull wire then extends through the lumen, including the two or more twisted regions. In this manner, the catheter will have three or more different curved regions, which may be coplanar or not, depending on the angles through which the twisted regions are curved.

The catheter shaft 16 preferably includes the one or more electrodes 14 disposed at strategically placed locations relative to the respective curved regions, such that when the pull wire is tensioned, the electrodes are deployed into operative positions for contacting a patient's tissue. One or more of the electrodes may be displaceable relative to the catheter shaft by a mandrel (not shown) which includes a first, proximal end securely connected to a slide actuator (not shown) or other suitable member formed on the handle 24. The mandrel extends distally from the slide actuator through the handle 24, through one of the lumen 22, and then extends laterally with respect to the catheter shaft and into engagement with the inside surface of the slidable electrode. Such a construction is disclosed in detail in U.S. patent application Ser. No. 09/203,922, and now U.S. Pat. No. 6,178,354, the disclosure of which is expressly incorporated herein by reference.

In one preferred embodiment, the distal portion of the medical device 10 is formed of a relatively flexible material and the pull wire 29 extends through a lumen located adjacent one selected side of the device, in order to facilitate bending of the distal end in the desired direction toward the selected side.

In operation, a clinician inserts the distal end of the catheter shaft 16 into a patient's blood vessels and manipulates the shaft through the vasculature to an intended site. As the catheter is manipulated through the vasculature, the clinician may periodically tension the pull wire 29 to impart a curve to the distal region of the catheter so that it may pass through curved regions within the patient's body (FIGS. 2 and 2A). In addition, once the catheter is disposed at the intended site within the patient, the pull wire 29 may be tensioned so that the catheter shaft 16 assumes the desired curvature, with one or more of the electrodes 14 carried along the catheter shaft being deployed into contact with a patient's tissue for diagnostic, therapeutic, and/or ablative procedures. Once the procedure or procedures are completed, the clinician then removes the catheter from the patient.

Thus, for example, the distal end region of the catheter may be designed so that it assumes a predetermined curve for manipulation purposes through the patient's vasculature, while one or more other catheter shaft regions may be designed so that they assume various curves for electrode deployment purposes and the like.

In addition, the pull wire 29 may be only slightly tensioned to impart a relatively small curve or bend to the distal end of the catheter shaft 16 for passing through the patient's vasculature. Then, once the distal end of the catheter is at the intended site, the pull wire may be fully tensioned to impart the full curve to the distal region of the catheter so that the electrodes 14 are in position for contact with the patient's tissue.

A preferred method of forming the medical device 10 will now be described. A straight shaft member is secured into two clamp members, one of which is rotatable relative to the other. Preferably, the clamps are spaced approximately 1.5 centimeters apart. The rotatable clamp is activated to begin rotating the shaft material. If the desired twist is 90°, the rotatable clamp preferably rotates the shaft more than 90°, for example, 100°, to compensate for rebound when the shaft is released. When the shaft is twisted through the appropriate angle, a heat gun or other heat source is used to heat the shaft to a predetermined temperature, for example, about 180–200° F. The shaft temperature is maintained at the desired heat for a period of time, for example, one minute. The heat is then removed, and the shaft allowed to cool. Once cooled, the clamps are released, and the shaft is suitable for use in the medical device 10 of the invention. It will be understood that the predetermined temperature to which the shaft is heated will vary depending on the material forming the shaft.

In the case of a shaft with a 180° degree twist, the shaft is preferably twisted during formation through an angle of approximately 190° to compensate for rebound when the shaft is released.

From the foregoing, it will be apparent to those skilled in the art that the present invention provides a medical device which includes a steering subsystem that facilitates manipulation of the medical device through a patient's vasculature, and which also facilitates deployment of one or more electrodes into contact with a patient's tissue. In addition, the medical device of the present invention includes a steering subsystem which uses a relatively small number of components.

Having thus described preferred embodiments of the present invention, it is to be understood that the above-described arrangements and systems are merely illustrative of the principles of the present invention, and that other arrangements and systems may be devised by those skilled in the art without departing from the spirit and scope of the invention as claimed below.

What is claimed is:

1. A catheter comprising:
    an elongated shaft including at least one non-axial lumen extending through the shaft and having a longitudinal axis, the shaft being twisted by rotation of a distal shaft portion relative to a proximal shaft portion about the longitudinal axis at a predetermined location a selected amount and at least one portion of the shaft distal of the predetermined location is not further twisted by rotation about the longitudinal axis, whereby the twisting causes the lumen distal of the predetermined location to become axially displaced;
    a pull wire extending through the lumen; and
    means for tensioning the pull wire to impart a desired curve to the shaft.

2. The catheter of claim 1, wherein the lumen is twisted approximately 90 degrees.

3. The catheter of claim 1, wherein the lumen is twisted approximately 180 degrees.

4. The catheter of claim 1, wherein the lumen is twisted less than 180 degrees.

5. The catheter of claim 1, wherein the lumen extends along the length of the shaft.

6. The catheter of claim 1, wherein the means for tensioning comprises a handle and a pull wire tensioning member mounted to the handle, wherein the tensioning member is manipulable relative to the handle, and wherein the pull wire is connected to the tensioning member, such that manipulation of the tensioning member tensions the pull wire.

7. The catheter of claim 1, wherein a proximal region of the catheter is formed of a composition having a first durometer, and a distal region of the catheter is formed of a composition having a second durometer different from the first durometer.

8. A medical device comprising:

a handle including a pull wire tensioning member, the pull wire tensioning member being manipulable relative to the handle;

an elongated shaft including at least one non-axial first lumen extending through the shaft and having a longitudinal axis, the shaft being formed at a predetermined location with a twist by rotation of a distal shaft portion relative to a proximal shaft portion about the longitudinal axis at a predetermined location a selected amount and at least one portion of the shaft distal of the predetermined location is not further twisted by rotation about the longitudinal axis, whereby the twisting causes the first lumen distal of the predetermined location to become axially displaced; and a pull wire extending through the first lumen, the pull wire being connected to the pull wire tensioning member, whereby manipulation of the pull wire tensioning member tensions the pull wire to induce a curve in the shaft.

9. The medical device of claim 8, wherein the shaft is twisted approximately 90 degrees.

10. The medical device of claim 8, wherein the shaft is twisted approximately 180 degrees.

11. The medical device of claim 8, wherein the shaft is twisted less than 180 degrees.

12. The medical device of claim 8, wherein the first lumen extend along the length of the shaft.

13. The medical device of claim 8 further including a second lumen axially displaced from the first lumen and wherein the portion of the catheter adjacent the first lumen is formed of a composition having a first durometer, and the portion of the catheter adjacent the second lumen is formed of a composition having a second durometer different from the first durometer.

14. A medical device comprising:

an elongated shaft including at least one non-axial first lumen extending through the shaft and having a longitudinal axis, the shaft being formed at a predetermined location with a twist by rotation of a distal shaft portion relative to a proximal shaft portion about the longitudinal axis at a predetermined location a selected amount and at least one portion of the shaft distal of the predetermined location is not further twisted by rotation about the longitudinal axis, whereby the twisting causes the first lumen distal of the predetermined location to become axially displaced; and a pull wire extending through the first lumen; and a control member operative to tension the pull wire to impart a desired curve to the shaft.

15. The medical device of claim 14, wherein the shaft is twisted approximately 90 degrees.

16. The medical device of claim 14, wherein the shaft is twisted approximately 180 degrees.

17. The medical device of claim 14 further including a second lumen axially displaced from the first lumen and wherein the portion of the catheter adjacent the first lumen is formed of a composition having a first durometer, and the portion of the catheter adjacent the second lumen is formed of a composition having a second durometer different from the first durometer.

18. The medical device of claim 14, wherein the medical device comprises a catheter.

19. A method of forming a medical device, comprising the steps of:

providing an elongated shaft with at least one non-axial lumen extending along the length of the shaft and the shaft having a longitudinal axis;

twisting the shaft by rotation of a distal shaft portion relative to a proximal shaft portion about the longitudinal axis at a predetermined location a selected amount and at least one portion of the shaft distal of the predetermined location is not further twisted by rotation about the longitudinal axis;

heating at least a portion of the shaft to at least a threshold temperature;

extending a pull wire through the lumen; and connecting the pull wire to a pull wire tensioning member.

* * * * *